United States Patent
Ravi et al.

(10) Patent No.: US 11,253,727 B2
(45) Date of Patent: Feb. 22, 2022

(54) MAGNETIC RESONANCE VISIBLE MARKERS FOR MAGNETIC RESONANCE IMAGING GUIDED BRACHYTHERAPY

(71) Applicant: Sunnybrook Research Institute, Toronto (CA)

(72) Inventors: Ananth Ravi, Toronto (CA); Moti Raj Paudel, Toronto (CA); Amir Owrangi, London (CA); Harry Easton, Toronto (CA)

(73) Assignee: Sunnybrook Research Institute, Toronto (CA)

( * ) Notice: Subject to any disclaimer, the term of this patent is extended or adjusted under 35 U.S.C. 154(b) by 159 days.

(21) Appl. No.: 16/755,973

(22) PCT Filed: Oct. 18, 2018

(86) PCT No.: PCT/CA2018/000197
§ 371 (c)(1),
(2) Date: Apr. 14, 2020

(87) PCT Pub. No.: WO2019/075548
PCT Pub. Date: Apr. 25, 2019

(65) Prior Publication Data
US 2020/0298021 A1  Sep. 24, 2020

Related U.S. Application Data

(60) Provisional application No. 62/573,972, filed on Oct. 18, 2017.

(51) Int. Cl.
*A61N 5/10* (2006.01)

(52) U.S. Cl.
CPC ......... *A61N 5/1039* (2013.01); *A61N 5/1001* (2013.01); *A61N 5/1049* (2013.01);
(Continued)

(58) Field of Classification Search
CPC .......... A61N 5/00; A61N 5/10; A61N 5/1039; A61N 5/1049; A61N 5/1001;
(Continued)

(56) References Cited

U.S. PATENT DOCUMENTS

| 8,529,872 B2 | 9/2013 | Frank et al. |
| 2014/0243655 A1 | 8/2014 | Goodwin |

(Continued)

FOREIGN PATENT DOCUMENTS

| EP | 2777767 A1 | 9/2014 |
| JP | H1014909 A | 1/1998 |
| WO | 2004105626 A2 | 12/2004 |

OTHER PUBLICATIONS

Beiki-Ardakani A, et al. Line Markers for MRI Only Brachytherapy. BRACHYTHERAPY 14. Jun. 2015.
(Continued)

*Primary Examiner* — Jurie Yun
(74) *Attorney, Agent, or Firm* — Quarles & Brady LLP

(57) ABSTRACT

Magnetic resonance ("MR") visible markers for use in MR-guided placement of brachytherapy seeds, and for use in other MR-guided interventional procedures, are described. The MR-visible markers generally include a tube in which an absorbent thread assembly is disposed. The tube is made fluid-tight by sealing it at both ends with suitable end plugs. The absorbent thread assembly is soaked in a suitable MR-visible fluid.

20 Claims, 4 Drawing Sheets

(52) U.S. Cl.
CPC ............... *A61N 2005/1009* (2013.01); *A61N 2005/1021* (2013.01); *A61N 2005/1051* (2013.01); *A61N 2005/1055* (2013.01)

(58) Field of Classification Search
CPC .... A61N 2005/1021; A61N 2005/1055; A61N 2005/1051; A61N 2005/1009; A61B 5/00; A61B 5/05; A61B 5/055; A61B 90/39; A61B 2090/3954; A61L 29/18
See application file for complete search history.

(56) References Cited

U.S. PATENT DOCUMENTS

| | | |
|---|---|---|
| 2015/0327949 A1 | 11/2015 | Van De Wardt et al. |
| 2016/0073925 A1 | 3/2016 | Grodzki et al. |

OTHER PUBLICATIONS

International Searching Authority, International Search Report and Written Opinion for application PCT/CA2018/000197, dated Jan. 24, 2019.
Owrangi AM, et al. Clinical implementation of MR-guided vaginal cylinder brachytherapy. J Appl Clin Med Phys 2015; 16: 490-500.
Tanderup, K. et al. Applicator reconstruction in cervix brachytherapy. 2009. available online; https://www.embracestudy.dk/UserUpload/PublicDocuments/Applicator%20reconstruction%20catalogue.PDF.

MAGNETIC RESONANCE VISIBLE MARKERS FOR MAGNETIC RESONANCE IMAGING GUIDED BRACHYTHERAPY

CROSS-REFERENCE TO RELATED APPLICATIONS

This application represents the national stage entry of PCT/CA2018/000197 filed Oct. 18, 2018, which claims the benefit of U.S. Provisional Patent Application 62/573,972, filed Oct. 18, 2017, which are incorporated by reference herein in their entirety for all purposes.

BACKGROUND

Magnetic resonance imaging ("MRI") is rapidly becoming a standard imaging tool in the arsenal to provide optimal image guidance for brachytherapy procedures. The reason for this increased use of MRI is because no other imaging modality is able to provide similar soft tissue contrast for the accurate delineation of cancerous lesions and normal tissue.

Brachytherapy is one of the most effective therapeutic techniques for the treatment of cancer, particularly prostate and gynecological cancers. It involves placing radioactivity in close vicinity to the tumor through implanted applicators and needles.

The implementation of MR-guided brachytherapy is hampered by difficulty in accurately visualizing and delineating the applicators within the patient. Plastic applicators do not produce an MR signal, and so these devices appear as voids in images obtained with MRI, while titanium applicators create artifacts in the image, whereby these artifacts erroneously localize the applicator. Depending on the image slice thickness, volume averaging for thick slices can degrade the contrast of the applicator rendering in indistinguishable from background. Also, the presence of anatomical features in the background that have similar image intensity values to the applicator voids can make it difficult to accurately delineate the applicator. As such, many MR images are often supplemented with CT images to aid in applicator reconstruction. But, this approach adds additional radiation dose to patients, prolongs the treatment planning process, and also adds to planning uncertainties due to the need for image co-registration.

Thus, using MRI alone is desirable; however, before this can be implemented routinely a robust and reproducible method for reconstructing the implanted applicators is needed.

In CT-based brachytherapy, radio-opaque markers are inserted into applicators to facilitate the delineation of applicators. In the MRI setting there are currently no markers that can reliably serve a similar purpose. Current commercially available MR applicator markers are very large and are only suitable for a small subset of applicators, precluding their use in brachytherapy procedures with needles (e.g., prostate and interstitial gynecological brachytherapy). Additionally, these markers require the user to fill them with a liquid media of their own choosing, which often results in air bubbles being trapped in the marker line. Air in the marker appears as a void. Thus, when these air bubbles are located at the tip of the applicator they result in the incorrect reconstruction of the applicator.

Thus, there remains a need for more robust MR-visible markers for use with the positioning and reconstruction of brachytherapy applicators.

SUMMARY OF THE DISCLOSURE

The present disclosure addresses the aforementioned drawbacks by providing a magnetic resonance visible marker including a tube, a proximal end plug, a distal end plug, and an absorbent thread assembly. The tube has a lumen and extends from a proximal end to a distal end along a length of the tube. The proximal end plug is arranged in the lumen at the proximal end of the tube to provide a fluid-tight seal at the proximal end of the tube, and the distal end plug is arranged in the lumen at the distal end of the tube to provide a fluid-tight seal at the distal end of the tube such that a fluid-tight volume is formed in the lumen between the proximal end plug and the distal end plug. The absorbent thread assembly spans the lumen of the tube from the proximal end plug to the distal end plug. The absorbent thread assembly has been soaked in and thereby absorbed a magnetic resonance visible fluid.

It is another aspect of the present disclosure to provide a method for manufacturing a magnetic resonance visible marker for use with a brachytherapy seed applicator. An absorbent thread assembly having a plurality of absorbent threads is soaked in a magnetic resonance visible fluid for a period of time. After the period of time, and while keeping the absorbent thread assembly and tube submerged in the magnetic resonance visible fluid, a leading end of the absorbent thread assembly is inserted into a first end of the tube, a syringe is coupled to a second end of the tube, and suction is applied to the tube via the syringe so as to pull the absorbent thread into the tube. The syringe is removed from the tube when the absorbent thread assembly reaches the second end of the tube, and the leading end of the absorbent thread assembly is pulled through the second end of the tube. The absorbent thread assembly is then trimmed to be flush with the first end and the second end of the tube. The first end of the tube is sealed using a first end plug and the second end of the tube is sealed using a second end plug.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
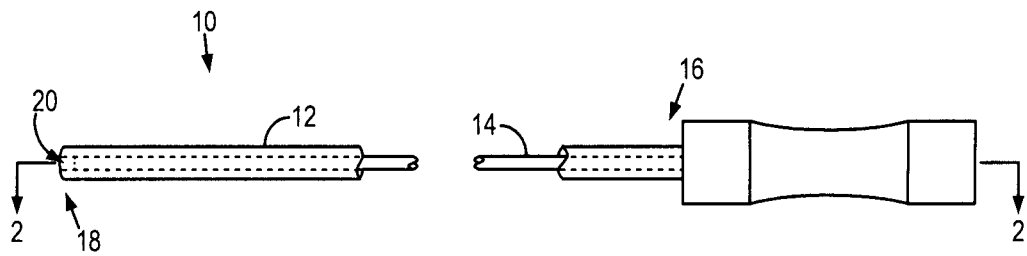
FIG. 1 shows an example of a magnetic resonance ("MR") visible marker for use with a brachytherapy applicator or other interventional device.

Described here are magnetic resonance ("MR") visible markers for use in MR-guided placement of brachytherapy seeds, and for use in other MR-guided interventional procedures. The MR-visible markers described in the present disclosure have broad applications in MR-guided interventional procedures, such as MR-guided brachytherapy and are constructed to be coupled to an interventional device, such as a brachytherapy seed applicator, catheter, or so on. Methods for manufacturing such MR-visible markers are also described in the present disclosure.

An MR-visible marker 10 generally includes a tube 12 in which an absorbent thread assembly 14 is disposed. The tube 12 extends from a proximal end 16 to a distal end 18 and is sealed at both its proximal end 16 and its distal end 18, thereby forming a closed volume in the lumen 20 of the tube 12 for containing the absorbent thread assembly 14. In some implementations, the tube 12 is sized to have a diameter that can fit any 5 or 6 French needle, which can be used for brachytherapy applications; however, in other constructions the tube 12 can have a different diameter.

The absorbent thread assembly 14 is soaked with an MR-visible fluid, such as water or a solution containing an MR-visible material such as a contrast agent, and placed in the tube 12. The absorbent thread assembly 14 is constructed to enable sufficiently even diffusion of the MR-visible fluid along the length of the absorbent thread assembly 14, which minimizes the likelihood of air leaking into the tube 12 where it would degrade the quality and accuracy of imaging the MR-visible marker 10.

Figure 2:
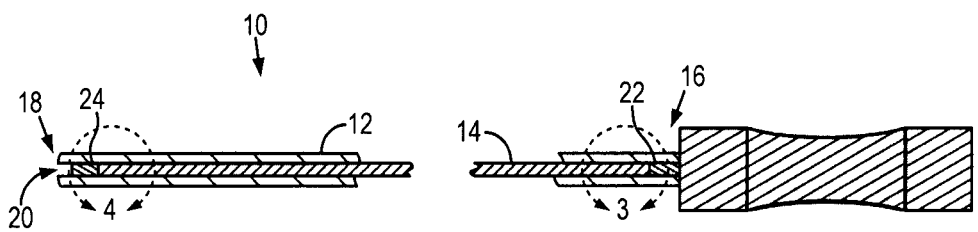
FIG. 2 shows a cross section through the MR-visible marker of FIG. 1.
Figure 3:
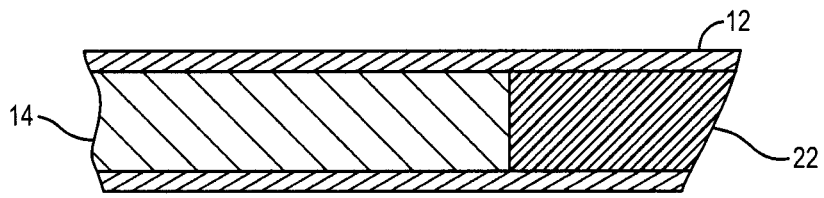
FIG. 3 shows a cutaway section of the proximal end of the MR-visible marker of FIGS. 1 and 2.
Figure 4:
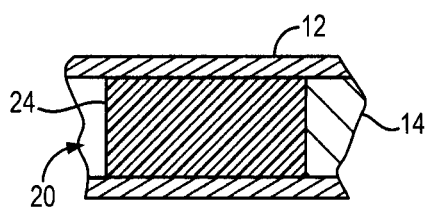
FIG. 4 shows a cutaway section of the distal end of the MR-visible marker of FIGS. 1 and 2.

As shown in FIGS. 2, 3, and 4, the tube 12 is sealed on both its proximal end 16 with a proximal end cap 22 and at its distal end 18 with a distal end cap 24 to ensure that air does not enter the tube 12 and interfere with the image contrast provided by the MR-visible marker 10, and also to reduce the risk of inaccurate reconstruction of the interventional device to which the MR-visible marker 10 may be coupled (e.g., a brachytherapy applicator). The tube 12 can be composed of a suitable biocompatible material, such as polyimide. In some implementations, the proximal end cap 22, the distal end cap 24, or both, can be pressure fit plastic end caps. As one non-limiting example, the proximal end cap 22, the distal end cap 24, or both, can be composed of polyether ether ketone ("PEEK"). The proximal end cap 22, the distal end cap 24, or both, can additionally be held in place in the lumen 20 of the tube 12 using an adhesive. As one example, the adhesive may be a slow setting epoxy, such as Loctite EA M-21HP (Henkel AG & Co., KGaA; Dusseldorf, Germany).

Figure 5:
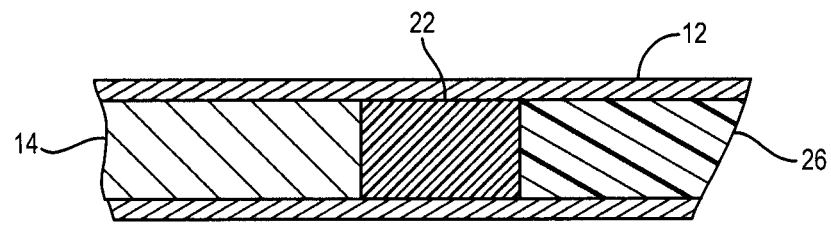
FIG. 5 shows a cutaway section of the proximal end of the MR-visible marker of FIGS. 1 and 2, in which both an end plug and an epoxy layer are used to seal the proximal end of the MR-visible marker.
Figure 6:
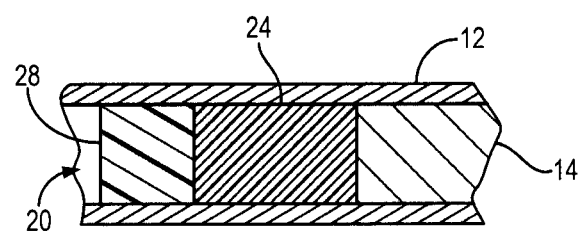
FIG. 6 shows a cutaway section of the distal end of the MR-visible marker of FIGS. 1 and 2, in which both an end plug and an epoxy layer are used to seal the distal end of the MR-visible marker.

The tube 12 can further be sealed at its proximal end 16 and its distal end 18 using an epoxy in addition to the proximal end cap 22 and the distal end cap 24. For instance, as shown in FIG. 5, an epoxy 26 can be provided to the lumen 20 of the tube 12 to further seal the proximal end 16 of the tube 12. In this example, the epoxy 26 is provided proximal to the proximal end cap 22. The epoxy 26 can be a thin epoxy that flows relatively easily (i.e., a low viscosity epoxy) and has a medium cure time (e.g., on the order of several hours at room temperature), such as EPO-TEK® 31 (Epoxy Technology, Inc.; Billerica, Mass.). Similarly, as shown in FIG. 6, the distal end 18 of the tube 12 can be further sealed by providing an epoxy 28 to the lumen 20 of the tube 12. In this example, the epoxy 28 is provided distal to the distal end cap 24. Like the epoxy 26 used to further seal the proximal end 16 of the tube 12, the epoxy 28 used to further seal the distal end 18 of the tube 12 can be a thin epoxy that flows relatively easily (i.e., a low viscosity epoxy) and has a medium cure time (e.g., on the order of several hours at room temperature), such as EPO-TEK® 31 (Epoxy Technology, Inc.; Billerica, Mass.).

As mentioned, the absorbent thread assembly 14 is provided an MR-visible fluid, such as by soaking the absorbent thread assembly 14 in the desired MR-visible solution. The MR-visible fluid can be water, a solution containing an MR-visible contrast agent, or other suitable MR-visible fluid. Examples of MR-visible fluids that can provide image contrast with T1-weighted pulse sequences include mineral oil (e.g., vitamin E), a solution containing gadolinium-based contrast agents, or a solution of copper(II) sulfate ($CuSO_4$) and saline (e.g., $CuSO_4$ plus an $NaCl_2$ solution in distilled water at a concentration sufficient to provide a positive magnetic resonance contrast). Examples of MR-visible fluids that can provide image contrast with T2-weighted pulse sequences include solutions containing superparamagnetic iron oxides ("SPIO") nanoparticles (e.g., BM547 BioMag® (Bang Laboratories, Inc.; Fishers, Ind.)).

In addition to selecting an MR-visible fluid that provides a desired image contrast, specialized magnetic resonance pulse sequences can be used to further enhance the observed contrast from the MR-visible marker 10. For instance, the effect of magnetic field inhomogeneities and susceptibility differences at the interface between the MR-visible marker 10 and the interventional device to which it is coupled can generate a measurable image contrast using susceptibility-weighted or other types of pulse sequences.

Figure 7:
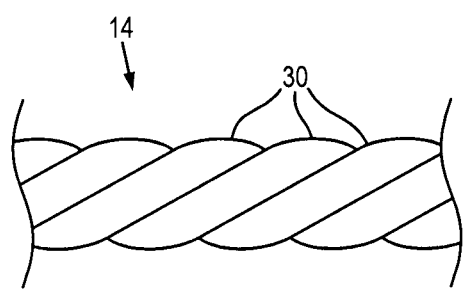
FIG. 7 shows one example of a section of an absorbent thread assembly for use in the MR-visible markers described in the present disclosure.

Referring now to FIG. 7, the absorbent thread assembly 14 generally includes a plurality of absorbent threads 30. The absorbent threads 30 are generally composed of hydrophilic materials, such that the absorbent threads 30 absorb and retain the MR-visible fluid. In some other implementations, the absorbent threads 30 can be composed of materials that are physically or chemically structured to trap and retain particles or fluids.

As one example, the absorbent threads 30 can be cotton threads. In some other embodiments, the absorbent threads 30 can be composed of other suitable absorbent materials, including natural fibers, such as wool, bamboo, hemp, or rayon; synthetic fibers, such as polyester or nylon; or composite fibers containing blends of different natural fibers, different synthetic fibers, or combinations of both natural and synthetic fibers. One example of an absorbent synthetic fiber is a microfiber thread containing split microfiber filaments, which can generally be composed of polyester, nylon, or other synthetic materials.

The absorbent threads 30 can be twisted to form the absorbent thread assembly 14, as shown in FIG. 7. For instance, the absorbent threads 30 can be twisted together using an S-twist or a Z-twist. In some other embodiments, the absorbent threads 30 do not need to be twisted together, but can be for example parallel, as shown in FIG. 8.

Figure 8:
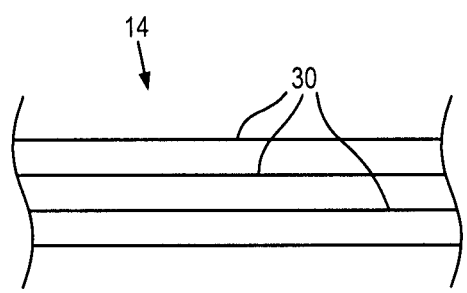
FIG. 8 shows another example of a section of an absorbent thread assembly for use in the MR-visible markers described in the present disclosure.
Figure 9A:
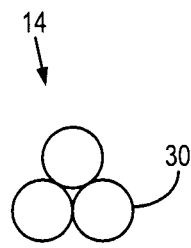
FIG. 9A shows one example of a cross section of an absorbent thread assembly for use in the MR-visible markers described in the present disclosure.
Figure 9B:
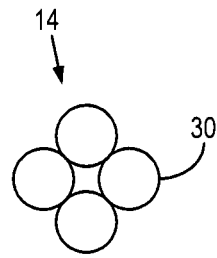
FIG. 9B shows another example of a cross section of an absorbent thread assembly for use in the MR-visible markers described in the present disclosure.
Figure 9C:
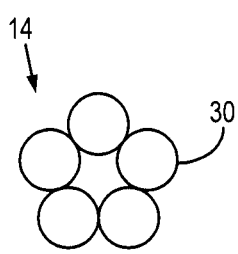
FIG. 9C shows another example of a cross section of an absorbent thread assembly for use in the MR-visible markers described in the present disclosure.
Figure 9D:
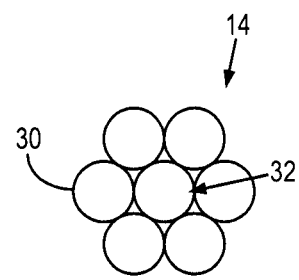
FIG. 9D shows another example of a cross section of an absorbent thread assembly for use in the MR-visible markers described in the present disclosure.

As shown in the example cross section of FIG. 9A, the absorbent thread assembly 14 can include three absorbent threads 30, which can be twisted as shown in FIG. 7 or not twisted as shown in FIG. 8. In other examples, the absorbent thread assembly 14 can contain fewer absorbent threads 30 (e.g., one or two), or more absorbent threads 30. FIGS. 9B and 9C show alternative examples of a cross section of an absorbent thread assembly 14 with more than three absorbent threads 30. In some other embodiments, one or more absorbent threads 30 can be twisted around one or more central absorbent threads 32, as shown in FIG. 9D. In the example cross section shown in FIG. 9D, the absorbent thread assembly 14 includes six absorbent threads 30 twisted around one central absorbent thread 32. It will be appreciated that other configurations of absorbent threads 30 other than those shown here can also be readily implemented.

Figure 10:
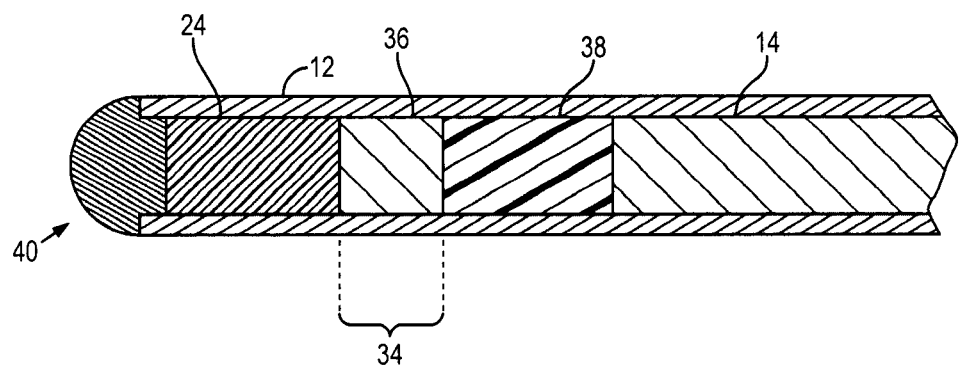
FIG. 10 is an example of an MR-visible marker according to some embodiments described in the present disclosure, in which the tube is partitioned into multiple different segments each containing a different absorbent thread assembly.

In some embodiments, the absorbent MR-visible marker 10 can include a segmented construction, as illustrated in FIG. 10. Such a construction facilitates detection and demarcation of the final dwell position of a brachytherapy source. In such examples, the tube 12 is partitioned to include one or more segments 34, each containing a different absorbent thread assembly segment 36. The one or more segments 34 are separated from the absorbent thread assembly 14 by a spacer 38 that is composed of a non-MR visible material, or a material having sufficiently different MR-visible signal intensity as the absorbent thread assembly 14 and absorbent thread assembly segment 36. In the example shown in FIG. 10, only one segment 34 is constructed; however, multiple different segments 34 could be constructed, each containing a different absorbent thread assembly segment 36 and separated by a different spacer 38. In these constructions, the absorbent thread assembly segment 36 can be the similarly constructed as the absorbent thread assembly 14, or can be constructed with different material properties (e.g., choice of absorbent thread material, number of threads).

The one or more segments 34 can be sized such that they are similarly dimensioned as the brachytherapy sources to be used. For instance, the one or more segments 34 could be 4 mm to 1 cm long when using an HDR brachytherapy source that is also 4 mm to 1 cm long. The position of the one or more segments 34 can also be offset relative to the tip 40 of the MR-visible marker 10, such that the position of the one or more segments 34 corresponds to the actual position of the brachytherapy source. The spacer 38 can be generally dimensioned to provide sufficient separation between the absorbent thread assembly segment 36 in the one or more segments 34 and the absorbent thread assembly 14, such that the absorbent thread assembly segment 36 can be visually distinguished from the absorbent thread assembly 14. As one example, the spacer 38 can be 1-2 cm long.

Figure 11:
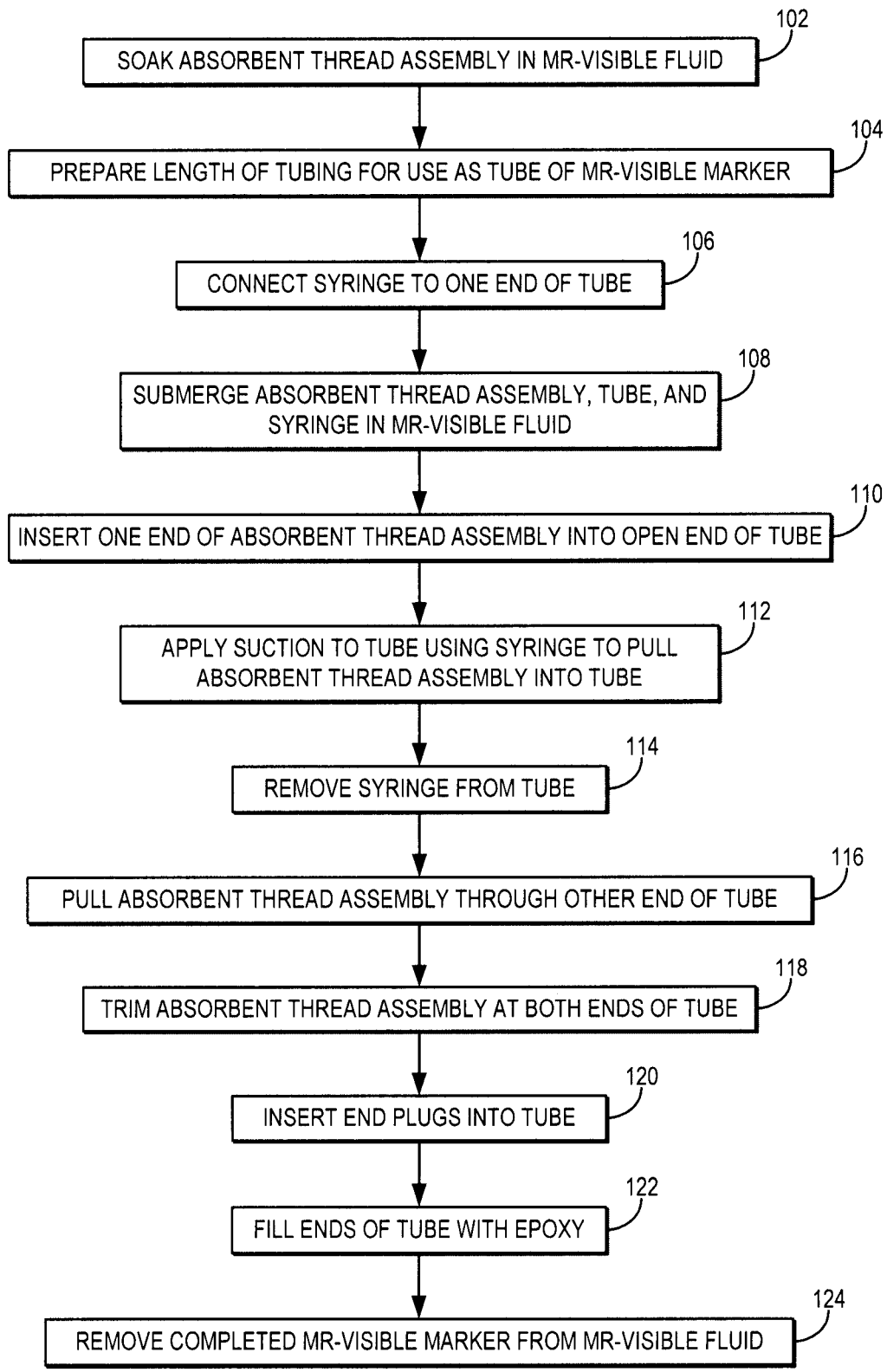
FIG. 11 is a flowchart setting forth the steps of an example method for manufacturing MR-visible markers according to some embodiments described in the present disclosure.

Having described examples of an MR-visible marker 10, a method for manufacturing such an MR-visible marker is now described. Referring to FIG. 11, a flowchart is illustrated as setting forth the steps of an example method for manufacturing an MR-visible marker as described in the present disclosure.

The method includes soaking an absorbent thread assembly 14 in an MR-visible fluid, such as those described above, for a prescribed period of time, as indicated at step 102. As one example, the absorbent thread assembly 14 can be soaked in the MR-visible fluid solution for a few hours or more. In some non-limiting examples, the absorbent thread assembly 14 can be soaked in the MR-visible fluid overnight.

A length of tubing is then prepared or otherwise provided, as indicated at step 104. For instance, a length of tubing can be cut to a desired length to form the tube 12 to be used for the MR-visible marker 10. As one non-limiting example, the tubing can be polyimide tubing, such as polyimide tubing sourced from Cole Palmer (part number 95820-11) with an outside diameter of 0.0540" and inside diameter of 0.0500".

The prepared length of tubing is snuggly connected to a syringe via an appropriately sized needle, as indicated at step 106. For instance, the polyimide tubing described above can be coupled to a 20 mL syringe via an 18 g needle. The tube 12, absorbent thread assembly 14, and needle are then submerged in the same MR-visible fluid in which the absorbent thread 14 was previously soaked, as indicated at step 108. One end of the absorbent thread assembly 14 is then inserted into an end of the tube 12, as indicated at step 110. To facilitate entry of the absorbent thread assembly 14 into the tube, the leading end of the absorbent thread assembly 14 can be cut on an angle before insertion into the tube.

After the leading end of the absorbent thread assembly 14 is inserted into the tube 12, suction is applied via the syringe to draw the absorbent thread assembly 14 into the tube 12, as indicated at step 112. When the absorbent thread assembly 14 reaches the syringe, the syringe is removed, as indicated at step 114, and the leading end of the absorbent thread assembly 14 is pulled through the other end of the tube 12, as indicated at step 116. For instance, tweezers may be used to pull the leading end of the absorbent thread assembly 14 through the other end of the tube 12. At this point, both end of the absorbent thread assembly 14 can be trimmed to be flush with the ends of the tube, as indicated at step 118.

A proximal end cap 22 and a distal end cap 24 are inserted into the respective ends of the tube 12 to close off any air ingress into the tube 12 and the absorbent thread assembly 14, as indicated at step 120. For instance, the proximal end cap 22 and the distal end cap 24 can each be inserted into the respective ends of the tube and pushed along the length of the tube 12 by approximately 2.0 mm. In a non-limiting example, the proximal end cap 22 and the distal end cap 24 can be PEEK plugs that are 2.0 mm (0.0787") long and 0.0505" in diameter. The proximal end cap 22 and the distal end cap 24 can be inserted into the ends of the tube 12 in conjunction with some slow setting epoxy, such as Loctite EA M-21HP. When the proximal end cap 22 and the distal end cap 24 are in position, the voids left at the ends of the tube 12 are filled with an epoxy to form a final seal, as indicated at step 122. As described above, the epoxy used in this step can be an EPO-TEK® 31 epoxy. At this point, the completed MR-visible marker 10 can be removed from the MR-visible fluid, as indicated at step 124.

The present disclosure has described one or more preferred embodiments, and it should be appreciated that many equivalents, alternatives, variations, and modifications, aside from those expressly stated, are possible and within the scope of the invention.

The invention claimed is:

1. A magnetic resonance visible marker, comprising:
    a tube having a lumen and extending from a proximal end to a distal end along a length of the tube;
    a proximal end plug arranged in the lumen at the proximal end of the tube to provide a fluid-tight seal at the proximal end of the tube;
    a distal end plug arranged in the lumen at the distal end of the tube to provide a fluid-tight seal at the distal end of the tube such that a fluid-tight volume is formed in the lumen between the proximal end plug and the distal end plug;
    an absorbent thread assembly spanning the lumen of the tube from the proximal end plug to the distal end plug, wherein the absorbent thread assembly has been soaked in and thereby absorbed a magnetic resonance visible fluid.

2. The magnetic resonance visible marker as recited in claim 1, wherein the absorbent thread assembly comprises a plurality of absorbent threads.

3. The magnetic resonance visible marker as recited in claim 2, wherein the plurality of absorbent threads are composed of a natural fiber material.

4. The magnetic resonance visible marker as recited in claim 3, wherein the plurality of absorbent threads are composed of cotton.

5. The magnetic resonance visible marker as recited in claim 2, wherein the plurality of absorbent threads are twisted together.

6. The magnetic resonance visible marker as recited in claim 2, wherein the absorbent thread assembly comprises three to five absorbent threads that are twisted together.

7. The magnetic resonance visible marker as recited in claim 1, wherein the magnetic resonance visible fluid is water.

8. The magnetic resonance visible marker as recited in claim 1, wherein the magnetic resonance visible fluid contains a magnetic resonance contrast agent.

9. The magnetic resonance visible marker as recited in claim 8, wherein the magnetic resonance contrast agent contains at least one of superparamagnetic iron oxide nanoparticles or gadolinium.

10. The magnetic resonance visible marker as recited in claim 1, wherein the magnetic resonance visible fluid is a solution of copper(II) sulfate and saline.

11. The magnetic resonance visible marker as recited in claim 1, wherein the proximal end plug and the distal end plug are composed of polyether ether ketone (PEEK).

12. The magnetic resonance visible marker as recited in claim 1, wherein the proximal end plug and the distal end plug are coupled to the lumen of the tube via an adhesive.

13. The magnetic resonance visible marker as recited in claim 12, wherein the adhesive is an epoxy.

14. The magnetic resonance visible marker as recited in claim 13, further comprising a second epoxy that is provided to the lumen distal to the distal end plug and to the lumen proximal to the proximal end plug.

15. The magnetic resonance visible marker as recited in claim 14, wherein the second epoxy is a low viscosity epoxy.

16. The magnetic resonance visible marker as recited in claim 1, wherein the tube is composed of a biocompatible material.

17. The magnetic resonance visible marker as recited in claim 16, wherein the tube is composed of polyimide.

18. A method for manufacturing a magnetic resonance visible marker for use with a brachytherapy seed applicator, the steps of the method comprising:
    submerging a tube in a magnetic resonance visible fluid;
    soaking an absorbent thread assembly comprising a plurality of absorbent threads in the magnetic resonance visible fluid for a period of time;
    after the period of time and while keeping the absorbent thread assembly and tube submerged in the magnetic resonance visible fluid:
        inserting a leading end of the absorbent thread assembly into a first end of the tube;
        coupling a syringe to a second end of the tube and applying suction to the tube via the syringe so as to pull the absorbent thread assembly into the tube;
        removing the syringe from the tube when the absorbent thread assembly reaches the second end of the tube and pulling the leading end of the absorbent thread assembly through the second end of the tube;
        trimming the absorbent thread assembly flush with the first end and the second end of the tube; and
        sealing the first end of the tube using a first end plug and the second end of the tube using a second end plug.

19. The method as recited in claim 18, wherein sealing the first end of the tube and the second end of the tube further comprises providing a low viscosity epoxy to the first end of the tube and to the second end of the tube.

20. The method as recited in claim 18, wherein the period of time is between four and twelve hours.

* * * * *